United States Patent [19]

Gruenenwald

[11] 4,236,523

[45] Dec. 2, 1980

[54] FREQUENCY TO VOLTAGE CONVERTER FOR CARDIAC COMMUNICATION SYSTEM

[75] Inventor: Stanley L. Gruenenwald, Minneapolis, Minn.

[73] Assignee: Medtronic, Inc., Minneapolis, Minn.

[21] Appl. No.: 958,202

[22] Filed: Nov. 6, 1978

[51] Int. Cl.³ .............................................. A61N 1/36
[52] U.S. Cl. ............................... 128/419 PT; 128/904
[58] Field of Search ............... 128/696, 697, 702, 703, 128/706, 708, 903, 904, 419 PT

[56] References Cited

U.S. PATENT DOCUMENTS

| | | | |
|---|---|---|---|
| 2,492,617 | 12/1949 | Boland et al. | 128/706 |
| 2,957,135 | 10/1960 | Gray | 324/78 |
| 3,099,800 | 7/1963 | Vinson et al. | 329/128 |
| 3,244,991 | 4/1966 | Hofman | 329/128 |
| 3,518,983 | 7/1970 | Jorgensen | 128/702 |
| 3,559,083 | 1/1971 | Crouse | 329/104 |
| 3,611,167 | 10/1971 | Calfee et al. | 329/106 |
| 3,614,641 | 10/1971 | Thompson et al. | 329/110 |
| 3,624,410 | 11/1971 | Bruckert | 307/234 |
| 3,729,676 | 4/1973 | Currie et al. | 128/706 |
| 3,743,952 | 7/1973 | Comley, Jr. et al. | 329/110 |
| 3,872,252 | 3/1975 | Malchman et al. | 128/419 PT |
| 3,885,552 | 5/1975 | Kennedy | 128/419 PT |
| 3,953,848 | 4/1976 | Dillman et al. | 128/903 |
| 4,022,970 | 5/1977 | Vandling | 358/298 |
| 4,035,787 | 7/1977 | Hornung | 340/228 R |
| 4,087,637 | 5/1978 | DeKonti | 128/697 |

Primary Examiner—William E. Kamm
Attorney, Agent, or Firm—R. Lewis Gable; Joseph F. Breimayer

[57] ABSTRACT

An accurate frequency to voltage converter for cardiac telemetry systems, in which converter charges are stored in response to selected intervals proportional to the period of an alternating input signal. Linearization of the output voltage as a function of input frequency characteristic is effectively and inexpensively achieved by charging a set of charging and voltage holding capacitors from a substantially constant voltage through a resistance such that capacitor terminal voltage rises as an exponential function of time. The reciprocal function of frequency as a function of period has a similarly shaped characteristic curve, and these function characteristics are effectively combined by the invention to generate the desired linear overall conversion function. Additionally, a controlled switching means is employed for alternately establishing a pair of signal path conditions, and this switching means has a definite internal ON resistance which prevents complete discharge of a charging and voltage holding capacitor in the time allowed. To alleviate a conversion inaccuracy which would accordingly otherwise result, an additional charging capacitor is connected directly to a means which periodically discharges the set of charging and holding capacitors.

16 Claims, 7 Drawing Figures

FREQUENCY TO VOLTAGE CONVERTER FOR CARDIAC COMMUNICATION SYSTEM

CROSS REFERENCE TO COPENDING APPLICATIONS

Attention is drawn to the following copending, commonly assigned applications, all filed on the same date, which further describe coronary data transmission systems in which the subject invention may be incorporated.

"CARDIAC PACEMAKER HAVING A RATE LIMIT", filed Nov. 6, 1978 in the names of David L. Thompson, Ray S. McDonald, and Yan Sang Lee and having Ser. No. 957,828;

"DEMAND CARDIAC PACEMAKER HAVING REDUCED POLARITY DISPARITY" filed Nov. 6, 1978 in the names of Gerome P. Hartlaub and Ray S. McDonald and having Ser. No. 957,812;

"DIGITAL CARDIAC PACEMAKER" filed Nov. 6, 1978 in the names of Gerome P. Hartlaub, Ray S. McDonald, and Martin A. Rossing and having Ser. No. 957,960;

"SYSTEM FOR DETECTING CARDIAC PACER PULSE" filed Nov. 6, 1978 in the name of Bud Bennett and having Ser. No. 957,815; and "PROGRAMMING AND MONITORING APPARATUS FOR PROGRAMMABLE PACING GENERATOR" filed Nov. 6, 1978 in the name of Robert Smith and having Ser. No. 958,063.

BACKGROUND OF THE INVENTION

The present invention relates generally to a cardiac telemetry system and, more particularly, to an FM demodulator, which may also be termed a frequency to voltage converter, for use in such a system.

Various systems have been proposed and developed for the transmission of information relating to coronary function to a remote point. The information related to coronary function may, for example, be an electrocardiogram (EKG) signal. Another example is a signal relating the functioning of an implanted cardiac pacemaker, for example the waveform or duration of a pulse generated by the implanted cardiac pacemaker.

Transmission of such information may, for example, be from an implanted device to a point just outside the patient's body. This may be accomplished by a radio frequency transmitter within the implanted device cooperating with a suitable external receiver, or, preferably, by an audio frequency oscillator exciting a coil functioning as the primary winding of a coupling transformer cooperating with an external pick up coil functioning as the coupling transformer secondary winding.

Another example of transmission of signals carrying information relating to coronary function is transmission to an entirely remote location, such as a hospital, via a radio or telephone communication link. In this instance, suitable sensing arrangements attached to the patient's body, which arrangement may be the inductive pick-up system mentioned just above, provide a suitable signal for transmission via the communication link to the remote location. At the remote location, the signal is suitably displayed, for example, by a strip chart recorder, and interpreted by qualified personnel who can then take appropriate action.

One particularly useful modulation technique in such systems is frequency modulation, particularly of an audio signal. For example, an audio carrier frequency of 1000 Hz might be employed, which is compatible with an ordinary telephone communication system. At the transmitting end of such a system, a suitable FM modulator, which may be termed a voltage to frequency converter, converts a signal waveform represented by a varying voltage into a signal of varying frequency. At the receiving end, a demodulator, which may be termed a frequency to voltage converter, is employed to reconstruct a replica of the original varying voltage waveform.

In such systems, it is desirable that highly effective frequency demodulators are employed. Two desirable qualities in a frequency demodulator are extremely rapid response to changes in input frequency so as to accurately reproduce the original signal waveform, and a broad input frequency range. Additionally, in order to avoid distortion in the replicated signal waveform, the demodulator should have a reasonably linear output voltage as a function of input frequency characteristic. Additionally, it is desirable that all of these objectives be met by a demodulator circuit of minimal complexity and cost.

However, typical signal waveforms encountered in cardiac telemetry systems place stringent demands on the elements of such systems, particularly on the demodulator elements thereof and particularly where an audio frequency carrier is selected and transmission is over a system of limited bandwidth, such as a telephone transmission channel. Typical signal waveforms include frequency components of only a few Hertz, as well as relatively high frequency components at the leading and trailing edges of pulse-like signal elements. In light of these requirements it is desirable to convey as much information as possible through an available channel. For in an audio frequency system having a carrier center frequency of 1000 Hz, it would be desirable to have a relatively broad input frequency range such that deviations of from $-50\%$ to $+100\%$, or from 500 Hz to 2000 Hz, are accurately demodulated.

A number of demodulators have heretofore been employed or proposed for these purposes. Before proceeding with specific examples, it should be noted that there are few FM demodulators available, particularly in the audio frequency range, which have the desired broad input frequency range. A range of $\pm 30\%$ is much more typical than $-50\%$ to $+100\%$. Additionally, a rapid response such that demodulator output voltage instantly follows changes in input frequency is unusual. Further, the problem of linearization is often not addressed in a cost effective manner. Considering some specific examples, in the cardiac function monitoring system disclosed in U.S. Pat. No. 3,885,552—Kennedy, a phase locked loop frequency demodulator is employed. In another approach, such as is exemplified by U.S. Pat. No. 3,099,800—Vinson et al, square wave pulses of varying duration depending upon the frequency of an incoming AC waveform are generated, and then integrated to provide a DC output. It will be appreciated that this typical approach in particular suffers the disadvantage, when employed in a cardiac signal telemetry system, of a lack of instantaneous response to input frequency changes. The output integration may occur over a period as long as ten cycles of the incoming waveform. One frequency demodulator of particular relevance with respect to certain aspects of the present invention is a video demodulator as disclosed in U.S. Pat. No. 3,614,641—Thompson et al. In the Thompson et al video demodulator, potentials are stored by capacitors in response to selected half periods of recorded FM signals, and whichever one of the stored potentials is indicative of the intelligence in the FM signal is selected for output. Of course there are other types of FM demodulator circuits, such as ratio detectors and discriminators, both of which employ resonant circuits tuned to a center frequency.

From these various prior art examples it can be seen that there remains a need for an FM demodulator especially suitable for use in combination with cardiac telemetry systems, and which effectively handles the signal waveforms found in such systems.

SUMMARY OF THE INVENTION

Accordingly, it is an object of the invention to provide an FM demodulator particularly suitable for use in combination with a coronary function telemetry system.

It is another object of the invention to provide such a demodulator which has a relatively broad input frequency range.

It is another object of the invention to provide such a demodulator which has an extremely fast response to changes in input frequency.

It is still another object of the invention to provide such a demodulator which produces an output voltage which is a fairly linear function of input frequency.

It is a more particular object of the invention to effectively implement an accurate FM demodulator wherein charges are stored in response to selected intervals proportional to the period of an alternating input signal.

It is still another object to accomplish all of the foregoing objects in a demodulator embodiment which is free of undue complexity and therefore highly reliable, and relatively low in cost.

Briefly stated, and in accordance with one aspect of the invention, these and other objects are accomplished by a demodulator, incorporated in a cardiac telemetry system, for converting the frequency of a frequency modulated alternating signal carrying information related to coronary function to a corresponding voltage. The demodulator includes a means for generating trigger signals, which may be short duration voltage spikes, at intervals proportional to the period of the alternating signal. The intervals proportional to the period may actually be equal to the period of the incoming alternating signal, or may be a multiple or sub-multiple thereof. The demodulator includes a means for initially discharging a capacitance in response to a trigger signal, which means may comprise a switching transistor having its collector and emitter terminals connected across a capacitance which is to be discharged. Additionally, there is included a means for charging a capacitance through a resistance from a substantially constant voltage source, whereby capacitor voltage rises in accordance with an exponential function of time, as is well known. The demodulator further includes a pair of charging and voltage holding capacitors and means for alternately selecting between a pair of signal path conditions affecting the charging and voltage holding capacitors in response to trigger signals. One of the signal path conditions is characterized by one of the charging and voltage holding capacitors being connected both to the means for initially discharging a capacitance and to the means for charging a capacitance. At the same time, the other of the charging and voltage holding capacitors is connected to the voltage output point. The other of the signal path conditions is characterized by the other of the charging and voltage holding capacitors being connected both to the means for initially discharging a capacitance and to the means for charging a capacitance, while at the same time the one of the charging and voltage holding capacitors is connected to the voltage output point.

In operation, while one of the charging and voltage holding capacitors is being charged to a voltage indicative of the length of a signal interval then in progress, the other charging and voltage holding capacitor is supplying an output voltage, representative of the duration of the last of the intervals, to the output point. Upon the occurrence of the next trigger signal, the roles of the two charging and voltage holding capacitors are reversed, and the other voltage holding capacitor is connected to the voltage output point. At the same time the one charging and voltage holding capacitor is quickly initially discharged by the means for initially discharging, and thereafter charged through the resistance from the substantially constant voltage source. This system thus accepts a broad input frequency range and responds essentially instantaneously to input frequency changes on a period by period basis.

A particular feature of the invention is the extremely effective, yet low cost, manner in which a linear output voltage as a function of input frequency function is realized. This advantageous aspect is a result of the exponential voltage as a function of time characteristic which results when a capacitor is charged from a voltage source through a resistance, in contrast to being charged from a constant current source where a linear voltage as a function of time characteristic would result. With the charging through a resistance in accordance with the invention, voltage is a non-linear (exponential) function of period. That is, a graph of voltage as a function of time is not a straight line. As period lengthens, voltage increases less rapidly. It should be kept in mind that, while the capacitors in the demodulator of the present invention are charged in response to input frequency period, the actual input characteristic of interest is the frequency. An additional relationship used to advantage in connection with this aspect of the invention is that frequency is the reciprocal of period. The reciprocal function is also a non-linear function and, when graphed, produces a curve of similar, although not identical, shape to the exponential function. As period lengthens, frequency decreases less rapidly. The present invention quite effectively and inexpensively provides an output voltage which is a fairly linear function of input frequency by virtue of the combination of the exponential capacitor voltage as a function of period characteristic and the reciprocal frequency as a function of period characteristic. This linearization is not precise, but nonetheless by careful selection of component values can be held within useful limits, for example one or two percent linearity over an input frequency range of 500 Hz to 2000 Hz.

In a specific practical implementation of the invention, a controlled switching means is employed for establishing the signal path conditions. Since mechanical switching means would be impractical for the relatively high frequencies employed, solid state switching means are employed, for example CMOS integrated circuit bilateral switches. These switches are characterized by a definite, non-zero, ON resistance which is effectively introduced in series in the connection of a charging and holding capacitor to the means for initially discharging a capacitance. As a result of the relatively short duration of the discharge pulse, the charging and voltage holding capacitor may not be completely discharged in the time allowed. As a result, because the charging and voltage holding capacitors are not beginning with zero volts, the accuracy of the conversion is not as accurate as it might otherwise be.

To overcome this particular problem, in accordance with the invention, an additional charging capacitor is connected directly to the means for initially discharging a capacitance, and to the means for charging a capacitance, without the intervention of any switching means. This additional charging capacitor is accordingly connected in parallel with whichever of the charging and voltage holding capacitors happens to also be connected to both the means for initially discharging a capacitance and to the means for charging a capacitance in accordance with the particular signal path condition then selected, (the term "parallel" here being employed loosely as the series switching means resistance does isolate the capacitors to some degree). The additional charging capacitor is thus substantially completely discharged each time. The terminal voltage on charging and voltage holding capacitors then follows the terminal voltage on the charging capacitor to a large degree.

The present invention additionally contemplates the methods of converting frequency to voltage which are implemented as briefly described above. In particular, a method for linearly converting the frequency of an alternating signal carrying information related to coronary function to a corresponding voltage includes the steps of initially discharging a capacitance and then charging the capacitance through a resistance from a substantially constant voltage for an interval proportional to the period of the alternating signal. A conversion method in accordance with the invention may include the additional steps of initially discharging and then charging another capacitance through a resistance from a substantially constant voltage source for an interval proportional to the period of the alternating signal, while at the same time providing the voltage on the one capacitance to an output point.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings, in which:

DESCRIPTION OF THE PREFERRED EMBODIMENTS

Figure 1:
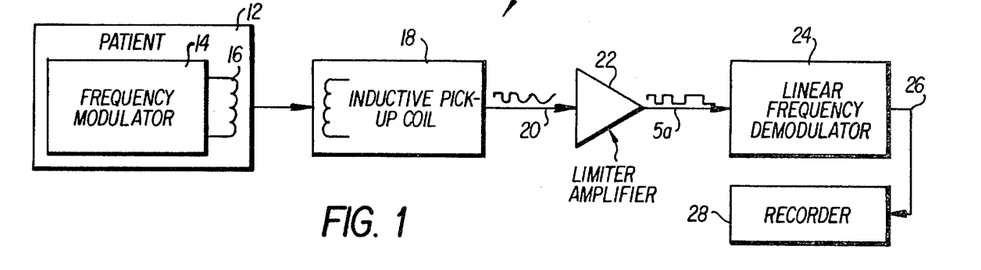
FIG. 1 is a block diagram of one form of coronary function telemetry system with which a demodulator according to the present invention may be employed in combination.

Referring now to the drawings, wherein identical reference numerals refer to corresponding elements in the several FIGS., in FIG. 1, the chain of a coronary function telemetry system generally designated 10 begins with a patient 12 having an implanted device comprising a frequency modulator 14. The input signal to the frequency modulator 14 may be any desired signal related to coronary function, for example an EKG signal or a signal indicative of implanted pacemaker operation. The frequency modulator 14 has an output link in the form of a coil 16 which serves as the primary winding of a signal coupling transformer. The frequency range applied to the coil 16 is preferably in the audio frequency range, but may as well be an RF carrier.

An inductive pick up coil 18, when placed in suitable proximity to the body of the patient 12 over the implanted device, functions as the secondary winding of a signal coupling transformer to receive signals transmitted by the coil 16. Instead of the inductive pick up coil 18, a suitable radio frequency receiver and demodulator may be employed if required by the specific frequency modulator used.

Figure 5A:
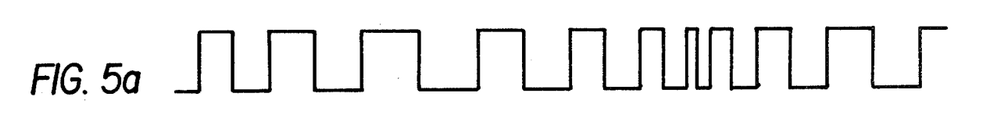
FIGS. 5a through 5h are voltage waveforms present during the operation of the exemplary circuit embodying the invention.

An output line 20 of the inductive pick up coil 18, carrying generally sine wave, frequency modulated signals, is applied to the input of a limiter amplifier 22 which squares up the signal to produce a square wave output waveform on line 5a. The signal on line 5a is also depicted by FIG. 5a.

The line 5a is applied to the input of a linear frequency demodulator 24 embodying the present invention. A voltage output of the linear demodulator 24 is connected via a line 26 to a suitable output device, such a strip chart recorder 28.

Figure 2:
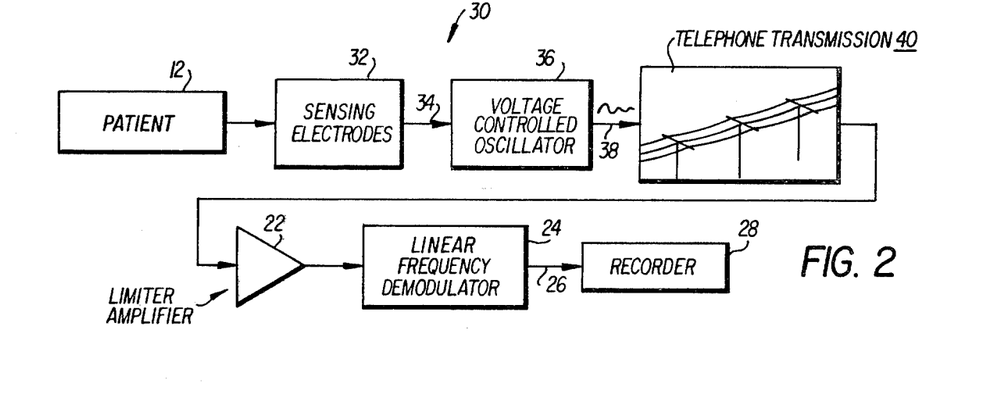
FIG. 2 is a block diagram of another such system.

Referring next to FIG. 2, an alternative coronary function telemetry system 30 includes sensing electrodes 32 which derive a signal carrying coronary-related information from the body of the patient 12. Many such electrode systems are known in the art, and will not be described here. The system 30 of FIG. 3 need not necessarily employ the sensing electrodes 32, but may as well employ a frequency modulator and inductive pickup coil system as in the system 10 of FIG. 1.

Still referring to FIG. 2, an output line 34 of the sensing electrodes 32 is applied to a conventional voltage controlled oscillator 36 which provides a frequency modulated sinewave on a line 38. This signal on line 38 is of a frequency range suitable for transmission over a telephone transmission system, as is represented at 40.

At the far end of the telephone transmission system 40 the limiter amplifier 22, linear frequency demodulator 24 in accordance with the invention, and strip chart recorder 28 may be connected.

In the operation of both the systems of FIGS. 1 and 2, a signal representative of a coronary function of particular interest within the body of the patient 12 is effectively transmitted through the respective system to be recorded by the recorder 28. The depictions of FIGS. 1 and 2 are by way of example only, and are no way exhaustive of the various possible configurations of cardiac telemetry systems employing linear frequency demodulators.

Figure 3:
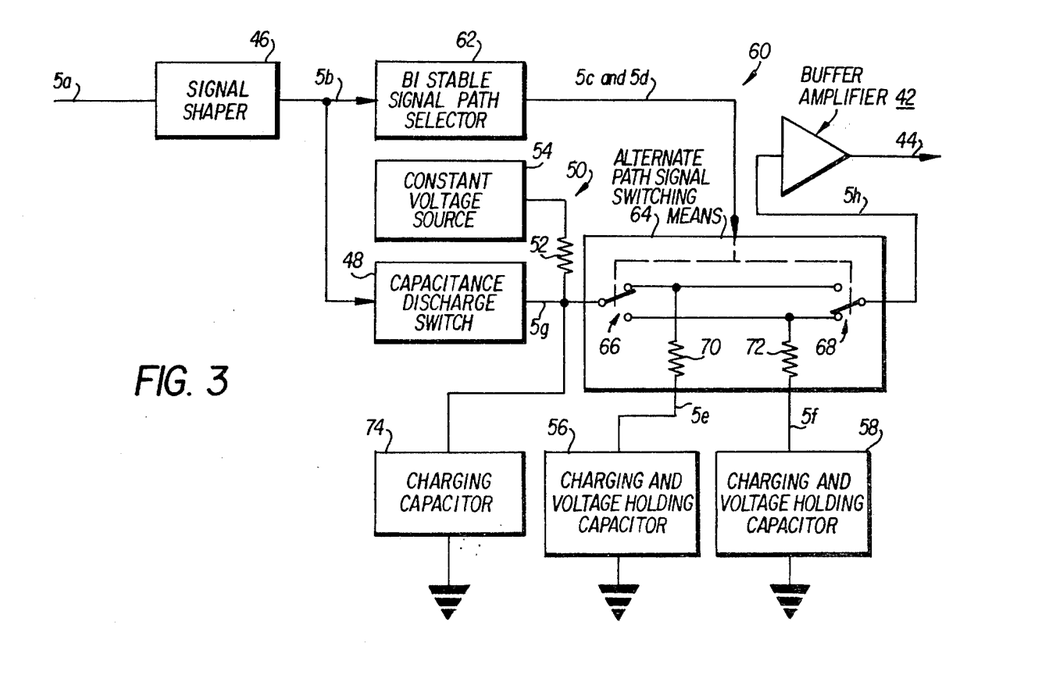
FIG. 3 is a block diagram of a linear demodulator constructed in accordance with the principles of the present invention.

With reference to FIG. 3, a block diagram of the frequency demodulator 24 is shown. The input point is the line 5a, previously mentioned with respect to FIGS. 1 and 2, carrying the waveform shown in FIG. 5a. A voltage output point or line of the demodulator 24 proper is designated 5h, with the signal thereon more particularly shown in FIG. 5h. A high input impedance buffer amplifier 42 has its input connected to the line 5h and supplies an actual output line 44.

In FIG. 3, a means for generating trigger signals at intervals proportional to the period of the alternating signal on the input line 5a comprises a signal shaper 46. The intervals proportional to the period of the alternating signal on the line 5a may be any multiple or sub-multiple of the actual period of the incoming signal but, preferably, are simply equal to each period. The term "period" is used herein in its usual sense as the time required for one complete cycle of the incoming square wave AC signal.

The output of the signal shaper 46 is the line 5b which is applied to the input of a means 48 for initially discharging a capacitance in response to a trigger signal, specifically a trigger signal on the line 5b. More particularly, the means 48 comprises a capacitance discharge switch.

In addition to the capacitance discharge switch 48, there is a means 50 for charging a capacitance through a resistance 52 from a substantially constant voltage source 54.

The capacitance discharge means 48 and the means 50 for charging a capacitance operate on a pair of charging and voltage holding capacitors 56 and 58, respective terminals of which are connected to lines 5e and 5f. To establish suitable connections to the charging and voltage holding capacitors 56 and 58, there is provided a means, generally designated 60, for alternately selecting between a pair of signal path conditions in response to trigger signals. More particularly, the means 60 comprises a bistable signal path selector 62 having its input connected to the line 5b from the signal shaper 46, and an alternate path signal switching means 64 responsive to the bistable signal path selector 62 via a line designated 5c & 5d.

One of the signal path conditions selected by the means 60 is characterized by the one capacitor 56 of the set of charging and voltage holding capacitors being connected both to the means 48 for initially discharging a capacitance and to the means 50 for charging a capacitance, while at the same time the other capacitor 58 of the charging and voltage holding capacitors is connected to the voltage output point comprising the line 5h. This signal path condition is established by switches 66 and 68, which are shown in this particular one signal path condition. The other of the signal path conditions is characterized by the other capacitor 58 of the charging and voltage holding capacitors being connected both to the means 48 for initially discharging a capacitance and to the means 50 for charging a capacitance, and the one capacitor 56 of the charging and voltage holding capacitors being connected to the voltage output point comprising the line 5h.

Figure 5B:
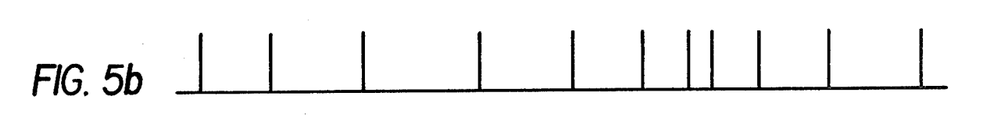
Figure 5C:
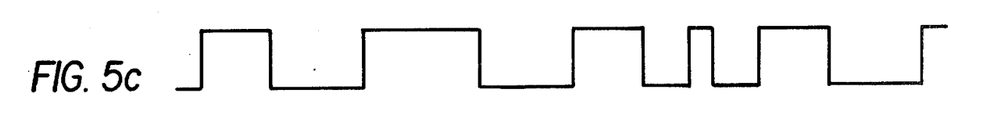
Figure 5D:
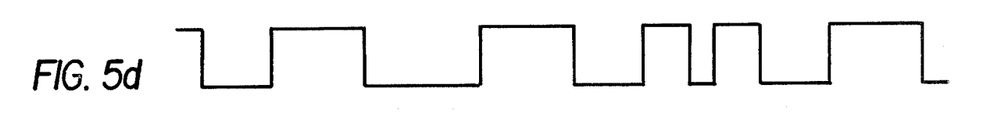

As a practical matter, it is a characteristic of the alternate path signal switching means 64 that a definite ON resistance is interposed in series in the connections to the charging and voltage holding capacitors 56 and 58. In FIG. 3, this switch ON resistance is represented by resistances 70 and 72. From FIG. 5b it can be seen that very little time is available for the capacitance discharge means 48 to discharge the charging and voltage holding capacitors 56 and 58. The internal resistances 70 and 72, by limiting current, prevent the complete discharge of these capacitors 56 and 58 within the time allowed. As a result, a slight residual voltage remains on these capacitors after intended discharge. This slight residual voltage would result in a degradation of conversion accuracy if not otherwise compensated for.

In accordance with the invention, an additional capacitor, termed a charging capacitor 74, is connected directly both to the means 48 for initially discharging a capacitance and to the means 50 for charging a capacitance. In particular, the direct connection to the discharging means 48, with substantially no series resistance, ensures that the charging capacitor 74 is almost completely discharged within the time allowed. To a certain degree then, the charging capacitor 74 is the primary one which is discharged and charged as the operational cycle proceeds, while the charging and voltage holding capacitors 56 and 58 tend somewhat to follow the voltage on the charging capacitor 74. This is particularly true upon the initial discharging of the capacitors.

Figure 4:
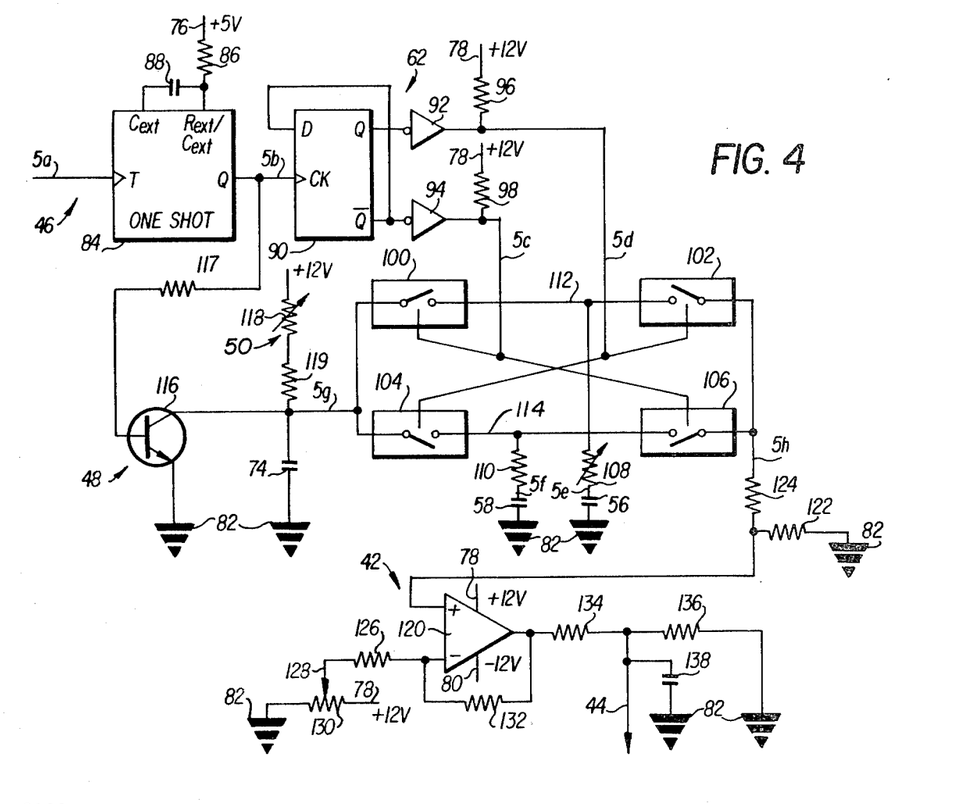
FIG. 4 is as exemplary schematic circuit diagram of a demodulator in accordance with the present invention, as is more generally represented in FIG. 3.

With reference now to FIG. 4, an actual schematic circuit diagram of the linear frequency demodulator 24 will be described. It should preliminarily be noted in connection with the circuit of FIG. 4, that suitable power supplies are required. As these power supplies are entirely conventional, they are not specifically shown but are merely represented as connection points. Specifically, a +5 volt supply is represented by a connection point 76, a +12 volt supply is represented by a connection point 78, and a −12 volt supply is represented by a connection point 80. All of these supply voltages are referenced to a common circuit reference point or ground 82. Additionally, it will be appreciated that the various integrated circuit devices shown functionally also require connections to appropriate supply voltages and to circuit ground, which connections are generally omitted for clarity of illustration.

The signal shaper 46 of FIG. 3 can more particularly be seen in FIG. 4 to comprise a monostable multivibrator configured as a one shot 84. The one shot 84, which may be a transistor transistor logic (TTL) integrated circuit device, has a trigger (T) input activated on low to high input signal transistions, and a Q output which goes high for the duration of an output pulse. Output pulse width is determined by a network comprising a resistor 86 and a capacitor 88 appropriately connected to the $C_{ext}$ and $R_{ext}/C_{ext}$ terminals. The output pulse width should be in the order of 5% of the period corresponding to approximately the center of the frequency range of interest. In the particular embodiment herein described, the pulse width is determined based on an appropriate center frequency of 1500 Hz. The corresponding period is 667 microseconds, and a 5% pulse is 33 microseconds in duration.

The bistable signal path selector 62 of FIG. 3 may more particularly be seen in FIG. 4 to comprise a D type flip-flop, which may also be a TTL device, having its $\overline{Q}$ output connected back to the D input in conventional configuration to establish divide-by-two operation. The flip-flop clock (CK) input receives the Q output from the one shot 84 via the line 5b. At the Q and $\overline{Q}$ outputs of the flip-flop 90, a pair of voltage level shifters comprising TTL inverters 92 and 94 with respective output pull-up resistors 96 and 98 connected to the +12 volt source 78 supply control lines 5c and 5d.

The control lines 5c and 5d are connected to the alternate path signal switching means 64 which may be seen in FIG. 4 to comprise four bilateral transmission gates or switches 100, 102, 104 and 106, which preferably are CMOS integrated circuit devices. Each of the bilateral switches 100, 102, 104 and 106 has a pair of switch terminals, and a single control input. To activate diagonally opposite pairs of the bilateral switches while the other two are inactive, the control inputs of the bilateral switches 100 and 106 are connected together and to the control line 5c, while the control inputs of the bilateral switches 102 and 104 are connected together and to the control line 5d. The the bilateral switches 100 and 104 of FIG. 4 together correspond to the switch 66 of FIG. 3, and the bilateral switches 102 and 106 of FIG. 4 together correspond to the switch 68 of FIG. 3.

The charging and voltage holding capacitors 56 and 58 of FIG. 3 also appear in FIG. 4 and are connected through respective series resistors 108 and 110 to lines 112 and 114 connecting upper and lower pairs of the bilateral switches. The internal resistances 70 and 72 of FIG. 3 are not specifically shown in FIG. 4, and will be understood to be internal to the bilateral switches 100, 102, 104 and 106. To complete the alternate path signal switching means 64, the left-hand terminals of the bilateral switches 100 and 104 are connected together and to the line 5g, and the right-hand terminals of the bilateral switches 102 and 106 are connected together and to the line 5h.

The means 48 of FIG. 3 for initially discharging a capacitance of FIG. 3 may be more particularly seen in FIG. 4 to comprise an NPN switching transistor 116 having its collector and emitter terminals connected across the charging capacitor 74, as well as across whichever of the charging and voltage holding capacitors 56 and 58 is selected by the switching means 64. The base terminal of the switching transistor 116 is connected through a current limiting resistor 117 to the line 5b connected to the Q output of the one shot 84.

The means 50 for charging a capacitance simply comprises a variable adjustment resistor 118 and a fixed resistor 119 connected in series between the +12 volt source 78 and the line 5g. The resistors 118 and 119 of FIG. 4 correspond to the resistance 52 of FIG. 3, while the +12 volt source 78 of FIG. 4 similarly corresponds to the constant voltage source 54 of FIG. 3.

At the output of the demodulator 24, the buffer amplifier 42 of FIG. 3 may be more particularly seen in FIG. 4 to comprise an operational amplifier 120 configured as a non-inverting high input impedance voltage buffer. For proper biasing of the operational amplifier 120, a high value input resistor 122 is connected between the non-inverting (+) input and circuit ground 82. In order to avoid unduly loading the charging and voltage holding capacitors 56 and 58, a resistor 124 of still higher value is connected between the voltage output point line 5h and the non-inverting (+) operational amplifier input.

For adjustable DC offset in the output of the operational amplifier 120, the inverting (−) input is connected through an input resistor 126 to the movable contact 128 of a potentiometer 130. The potentiometer 130 is suitably connected to bias the inverting (−) input at any level between circuit ground and +12 volts. To establish the gain of the buffer amplifier 42, a negative feedback resistor 132 having the same resistance as the input resistor 126 is connected between the operational amplifier 120 output and the inverting (−) input.

Lastly, a voltage divider comprising resistors 134 and 136 is connected to the output of the operational amplifier 120. The junction of the resistors 134 and 136 then supplies the output line 44. In order to minimize the effect of sharp output transitions which might otherwise result, a smoothing capacitor 138 may optionally be provided between the output line 44 and circuit to ground 82. This smoothing capacitor 138 may be required depending upon the response characteristics of the particular device connected to the line 44, for example a strip chart recorder.

The operation of the demodulator 24 of FIG. 4 may best be understood with reference to the waveforms of FIGS. 5a through 5h which, as suggested above, correspond to signal lines designated 5a through 5h in FIG. 4. The square wave input signal line 5a triggers the one shot 84 on each low to high transition of the input signal, producing trigger signals on the line 5b at intervals controlled by the period of the line 5a input line. The flip-flop 90 toggles each time it is clocked, causing the Q and $\overline{Q}$ outputs to each alternate between high and low. The inverters/level shifters 92 and 94 supply the control lines 5c and 5d with respective control signals which are 180° out of phase, as may be seen from FIGS. 5c and 5d. Initially, when 5c is high and 5d is low, the diagonally opposite bilateral switches 100 and 106 are ON, and the diagonally opposite bilateral switches 102 and 104 are OFF. The one charging and voltage holding capacitor 56 is accordingly effectively connected through the bilateral switch 100 to the line 5g, while the other charging and voltage holding capacitor 58 is connected through the bilateral switch 106 to the output line 5h.

Figure 5E:
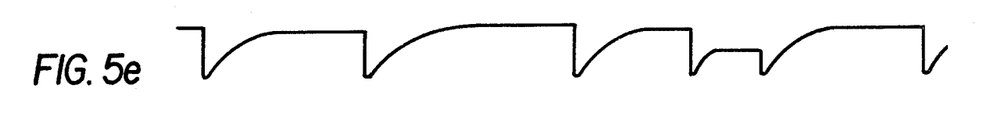

As indicated by the waveform of FIG. 5e, the one charging and voltage holding capacitor 56 is initially discharged through the switching transistor 116 as the transistor 116 is biased into conduction by the trigger signal on line 5b. As represented by the rounded lower tip of the FIG. 5e waveform, this discharge of the charging and voltage holding capacitor 56 does not reduce the voltage on the line 5e completely to zero. This is due to the various resistances interposed in series between the charging and voltage holding capacitor 56 and the transistor 116, including the compensation resistor 108 and the internal resistance of the bilateral switch 100.

During the interval while the control line 5c remains high, the charging and voltage holding capacitor 56 charges through the resistors 118 and 119 and through the bilateral switch 100 up towards +12 volts. As can be seen from FIG. 5e, the resultant voltage waveform is the familiar exponential resistance/capacitance charging characteristic.

At the same time, the potential on the other charging and voltage holding capacitor 58 is supplied through the bilateral switch 106 to the voltage output point 5h. The voltage waveform on this capacitor is shown in FIG. 5f.

The other signal path is selected when the line 5d is high, the line 5c is low, the bilateral switches 104 and 102 are ON, and the bilateral switches 100 and 106 are OFF. In this condition, the operation with respect to the two charging and voltage holding capacitors 56 and 58 is simply reversed, as may be seen from an examination of the waveforms of FIGS. 5a through 5h, and will not be further described.

At the same time the charging and voltage holding capacitors 56 and 58 are going through alternate charge/discharge/hold cycles, the charging capacitor 74 is going through alternate discharge/charge cycles, with no hold stage, in coincidence with whichever of the charging and voltage holding capacitors 56 and 58 is at that time connected to the line 5g. This action will be understood from an examination of FIG. 5g.

Figure 5F:
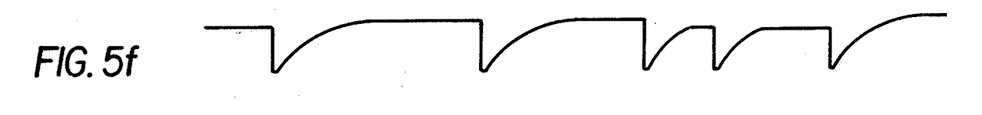
Figure 5G:
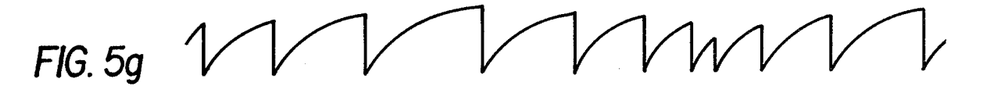

In FIG. 5g, the lower peaks of the discharge waveform are much sharper than those of FIGS. 5e and 5f due to their being substantially no series resistance interposed between the charging capacitor 74 and the switching transistor 116. The resultant voltage on the charging capacitor 74 thus more accurately represents the period of the incoming waveform, and the connected charging and voltage holding capacitor 56 or 58 simply follows. The ratios of the capacitances of the charging capacitor 74 to the capacitances of the charging and voltage holding capacitors 56 and 58 is not particularly critical, and these capacitors may all have equal values. However, if desired, the capacitance of the charging capacitor 74 may be greater than the capacitances of the charging and voltage holding capacitors 56 and 58.

The internal resistances of the bilateral switches 100, 102, 104 and 106 vary from one switch to the next. In order to avoid inaccuracies in the conversion process which might otherwise result, the resistor 108 in series with the one charging and voltage holding capacitor 56 is adjustable. In the adjustment procedure, the incoming waveform is held at a constant frequency (and period), and the resistor 108 is adjusted until the output voltage waveform is flat.

It will be appreciated that the provision of the charging capacitor 74 in accordance with the invention facilitates and makes possible such adjustment means without further degradation of the operation, for the same reason, discussed above, that the provision of the charging capacitor 74 greatly compensates for the internal resistances of the bilateral switches 100, 102, 104 and 106 in the first place.

Figure 6:
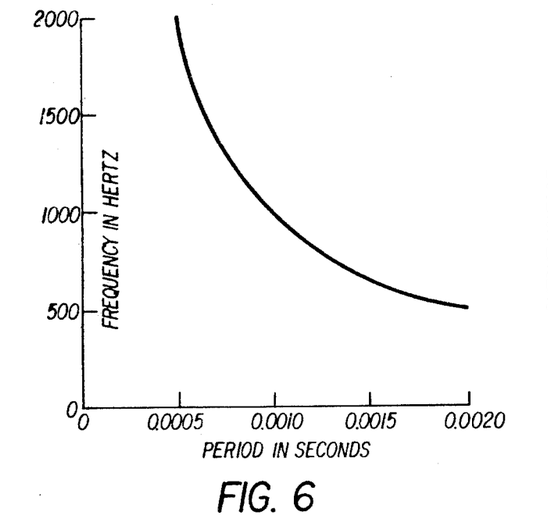
FIG. 6 is a graph showing the shape of the characteristic curve of frequency as a function of period, which is a reciprocal function.
Figure 7:
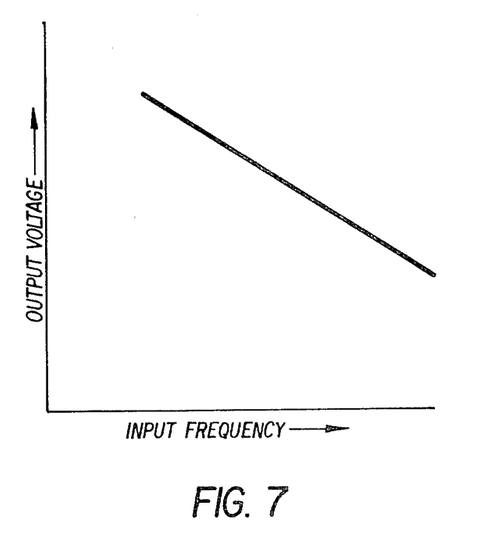
FIG. 7 is a graph generally depicting the linear output voltage as a function of input frequency characteristic which is realized by the present invention.

Considering now the operation of the linearization aspect of the invention, the familiar exponential voltage as a function of time curve of a capacitor charging through a resistance is shown as portions of FIGS. 5e, 5f and 5g. In FIG. 6, a reciprocal function curve of frequency as a function of period is shown, where frequency in Hertz is quite simply one divided by the period in seconds. While the exponential and reciprocal function curves are not identical, it can be seen by comparison of either FIGS. 5e, 5f or 5g with FIG. 6 that they are similar. In the operation of the circuit, these two curve types effectively cancel each other out, resulting in the approximately linear output voltage as a function of input frequency characteristic as is represented in FIG. 7. More specifically, from FIGS. 5e, 5f and 5g it can be seen that voltage is a non-linear function of period such that as period lengthens, voltage increases less rapidly. Similarly, from FIG. 6 frequency is a non-linear function of period such that as period lengthens, frequency decreases less rapidly.

Figure 5H:
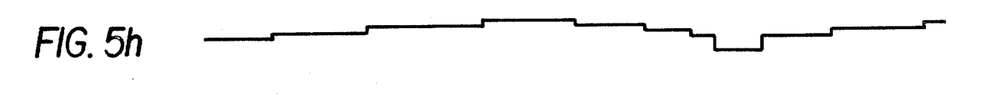

In this particular circuit, as is apparent from either a comparison of FIGS. 5a and 5h, or from FIG. 7 alone, the sign of the output voltage as a function of input frequency is negative. That is, as frequency increases, output voltage decreases. However, it will be apparent that this is a mere design choice. The sign may easily be reversed, for example by rearranging the circuit of the operational amplifier 120 in as inverting configuration.

Similarly, the offset from zero of the output voltage is entirely arbitrary. For example, in the circuit of FIG. 4, the setting of the potentiometer 130 varies this relationship as desired. In other words, for initial calibration or setting up of a complete system, any arbitrary output voltage may be set to correspond with a particular input frequency by simply adjusting the movable contact 128 of the potentiometer 130.

The following component values have been found suitable for use in the circuit of FIG. 4. It will be appreciated that these component values are exemplary only, and are not intended to limit the scope of the claimed invention. It will especially be appreciated that these values may be appropriately scaled where a different input frequency range is of interest.

TABLE

|  |  |
| --- | --- |
| Resistors | |
| 86, 126, 132, 134 | 10 K Ohms |
| 96, 98, 110, 136 | 1 K Ohms |
| 108, 118 | 10 K Ohms variable |
| 117 | 2 K Ohms |
| 119 | 100 Ohms |
| 122 | 1 Meg Ohm |
| 124 | 2 Meg Ohm |
| 130 | 10 K Ohm potentiometer |
| Capacitors | |
| 56, 58, 74 | 0.1 mfd. |
| 138 | 10 mfd. |
| 88 | .068 mfd. |
| Semiconductor Devices | |
| 84 | ½ of Texas Instruments Type No. SN74123 dual monostable multivibrator TTL integrated circuit |
| 90 | ½ of Texas Instruments Type No. SN7474 dual D-type flip-flop TTL integrated circuit |
| 92, 94 | Each is ¼ of a Texas Instruments Type No. SN7402 quad 2-input NOR gate TTL integrated circuit, with NOR gate inputs tied together |
| 100, 102, 104, 108 | Each is ¼ of an RCA Type No. CD4066 COS/MOS Quad Bilateral Switch, or alternatively RCA Type No. CD4016 |
| 116 | 2N3904 transistor |
| 120 | Motorola Type No. MC1536 integrated circuit operational amplifier |

In addition to varying the component values, it will be appreciated that numerous other changes may be made in the circuit without departing from the scope of the invention. As one example, instead of returning the lower terminal of the capacitors 74, 56 and 58 to the circuit ground point 82, they may as well be connected to the +12 volt source 78, with no alteration in circuit function. The active terminal voltages of these capacitors would behave in exactly the same manner. Of course, as a matter of nomenclature, whereas before the capacitor terminal voltages decreased with respect to the ground reference point as the capacitor was discharging, in the alternative herein proposed, as the capacitor terminal voltages decrease with respect to the ground reference point 82, the capacitors themselves would actually be charging. Accordingly, the terms charging and discharging of capacitors as herein employed are intended to refer to states of capacitor charge when referenced to ground. These terms should of course be read in the opposite sense where the capacitors are alternatively connected as just described.

Further, the information relating to coronary function may be a mode programming command or an acknowledgment thereof such as may be exchanged between an external programmer and an implanted device. An example of such a system is disclosed in the above-mentioned Smith application entitled "Programming and Monitoring Apparatus For Programmable Pacing Generator". Accordingly, the expression "information relating to coronary function" as employed in the specification and claims herein is intended to encompass any and all information which may be transmitted in a system having some connection to a heart.

It will be apparent therefore that has been provided a relatively uncomplicated, and yet highly effective, voltage to frequency converter especially suited to use in a cardiac telemetry system. More particularly, the complete discharging of capacitors for each input sampling period ensures that the output voltage very rapidly follows changes in input frequency. Additionally, linearization of the output voltage versus input frequency characteristic is effectively accomplished. Lastly, an effective solution to the practical problem caused by the series resistance of available solid state bilateral switches has been described.

While specific embodiments of the invention have been illustrated and described herein, it is realized that modifications and changes will occur to those skilled in the art to which the invention pertains. It is therefore to be understood that the appended claims are intended to cover all such modifications and changes as fall within the true spirit and scope of the invention.

What is claimed is:

1. In a system operatively connected to a heart, a demodulator for converting the frequency of a frequency modulated alternating signal carrying information related to coronary function to a corresponding voltage, said demodulator comprising:
   a voltage output point;
   means for generating trigger signals at intervals proportional to the period of the alternating signal;
   means for initially discharging a capacitance in response to a trigger signal;
   means for charging a capacitance through a resistance from a substantially constant voltage source;
   a pair of charging and voltage holding capacitors; and
   means for alternately selecting between a pair of signal path conditions in response to the trigger signals, one of said signal path conditions being characterized by one of said charging and voltage holding capacitors being connected both to said means for initially discharging a capacitance and to said means for charging a capacitance and the other of said charging and voltage holding capacitors being connected to said voltage output point, and the other of said signal path conditions being characterized by said other of said charging and voltage holding capacitors being connected both to said means for initially discharging a capacitance and to said means for charging a capacitance and said one of said charging and voltage holding capacitors being connected to said voltage output point.

2. A coronary function signal demodulator according to claim 1, which further comprises:
   a charging capacitor connected both to said means for initially discharging a capacitance and to said means for charging a capacitance.

3. A coronary function signal demodulator according to claim 1, wherein the rate at which said means for charging capacitance charges the capacitors is selected such that the resultant capacitor voltage at the end of each of the intervals is a substantially linear function of the frequency of the alternating signal.

4. A coronary function signal demodulator according to claim 1, wherein said means for selecting includes a controlled switching means for establishing the signal path conditions.

5. A coronary function signal demodulator according to claim 4, wherein:
   said controlled switching means introduces series resistance in the connection of a charging and holding capacitor to said means for initially discharging a capacitance such that the charging and holding capacitor is not completely discharged within the time available; and
   which demodulator further comprises a charging capacitor connected both directly to said means for initially discharging a capacitance and to said means for charging a capacitance.

6. A coronary function signal demodulator according to claim 5, wherein the rate at which said means for charging capacitance charges the capacitors is selected such that the resultant capacitor voltage at the end of each of the intervals is a substantially linear function of the frequency of the alternating signal.

7. A coronary function signal demodulator according to claim 5, which further comprises adjustable resistance means connected in series with at least one of said charging and voltage holding capacitors for compensating for unequal path resistances introduced by said controlled switching means.

8. In a system operatively connected to a heart, a demodulator for converting the frequency of a frequency modulated alternating signal carrying information related to coronary function to a corresponding voltage, said demodulator comprising:
   a voltage output point;
   means for generating trigger signals at intervals proportional to the period of the alternating signal;
   means for initially discharging a capacitance in response to a trigger signal;
   means for charging a capacitance as a function of time;
   a pair of charging and voltage holding capacitors; and
   means for alternating selecting between a pair of signal path conditions in response to trigger signals, one of said signal path conditions being characterized by one of said charging and voltage holding capacitors being connected both to said means for initially discharging a capacitance and to said means for charging a capacitance and the other of said charging and voltage holding capacitors being connected to said voltage output point, and the other of said signal path conditions being characterized by said other of said charging and voltage holding capacitors being connected both to said means for initially discharging a capacitance and to said means for charging a capacitance and said one of said charging and voltage holding capacitors being connected to said voltage output point.

9. A coronary function signal demodulator according to claim 8, which further comprises:

a charging capacitor connected both to said means for initially discharging a capacitance and to said means for charging a capacitance.

10. A coronary function signal demodulator according to claim 8, wherein the rate at which said means for charging capacitance charges the capacitors is selected such that the resultant capacitor voltage at the end of each of the intervals is a substantially linear function of the frequency of the alternating signal.

11. A coronary function signal demodulator according to claim 8, wherein said means for selecting includes a controlled switching means for establishing the signal path conditions.

12. A coronary function signal demodulator according to claim 11, wherein:

said controlled switching means introduces series resistance in the connection of a charging and holding capacitor to said means for initially discharging a capacitance such that the charging and holding capacitor is not completely discharged within the time available; and which demodulator further comprises a charging capacitor connected both directly to said means for initially discharging a capacitance and to said means for charging a capacitance.

13. In a system operatively connected to a heart, a demodulator for converting the frequency of a frequency modulated alternating signal carrying information related to coronary function to a corresponding voltage, said demodulator comprising:

a voltage output point;

means for initially discharging a capacitance in response to a trigger signal;

means for charging a capacitance through a resistance from a substantially constant voltage source;

a pair of charging and voltage holding capacitors; and means for alternately selecting between a pair of signal path conditions at intervals proportional to the period of the alternating signal, one of said signal path conditions being characterized by one of said charging and voltage holding capacitors being connected both to said means for initially discharging a capacitance and to said means for charging a capacitance and the other of said charging and voltage holding capacitors being connected to said voltage output point, and the other of said signal path conditions being characterized by said other of said charging and voltage holding capacitors being connected both to said means for initially discharging a capacitance and to said means for charging a capacitance and said one of said charging and voltage holding capacitors being connected to said voltage output point.

14. A coronary function signal demodulator according to claim 13, which further comprises:

a charging capacitor connected both to said means for initially discharging a capacitance and to said means for charging a capacitance.

15. A method for converting the frequency of an alternating signal carrying information related to coronary function to a corresponding voltage, which method comprises:

initially discharging a capacitance; and charging the capacitance through a resistance from a substantially constant voltage source for an interval proportional to the period of the alternating signal;

whereby the resultant voltage on the capacitance is an approximately linear function of input frequency.

16. A method according to claim 15, which further comprises, following the step of charging the capacitance, the additional step of:

initially discharging and then charging another capacitance through a resistance from a substantially constant voltage source for an interval proportional to the period of the alternating signal, while at the same time providing the voltage on the one capacitance to an output point.

* * * * *

UNITED STATES PATENT AND TRADEMARK OFFICE
CERTIFICATE OF CORRECTION

PATENT NO. : 4,236,523
DATED : December 2, 1980
INVENTOR(S) : Stanley L. Gruenenwald It is certified that error appears in the above-identified patent and that said Letters Patent are hereby corrected as shown below:

Column 14, Claim 8, Line 50: "means for alternating selecting"

should read --means for alternately selecting --

Signed and Sealed this

Tenth Day of March 1981

[SEAL]

Attest:

RENE D. TEGTMEYER

Attesting Officer    Acting Commissioner of Patents and Trademarks